United States Patent
Ericsson

(10) Patent No.: US 6,743,411 B2
(45) Date of Patent: Jun. 1, 2004

(54) EXTRACORPORAL SYSTEM FOR TREATING DISEASE WITH RADIONUCLEOTIDES

(75) Inventor: Arthur Dale Ericsson, Houston, TX (US)

(73) Assignee: RX/IBR Corporation, Houston, TX (US)

(*) Notice: Subject to any disclaimer, the term of this patent is extended or adjusted under 35 U.S.C. 154(b) by 98 days.

(21) Appl. No.: 09/938,884

(22) Filed: Aug. 24, 2001

(65) Prior Publication Data

US 2002/0004030 A1 Jan. 10, 2002

Related U.S. Application Data

(63) Continuation-in-part of application No. 09/183,454, filed on Oct. 30, 1998.

(51) Int. Cl.[7] .......................... A61K 51/00; A61M 36/14
(52) U.S. Cl. .................... 424/1.49; 424/1.11; 424/1.65; 424/9.1; 424/9.2
(58) Field of Search .............................. 424/1.11, 1.49, 424/1.65, 9.1, 9.2; 530/387.1, 387.2

(56) References Cited

U.S. PATENT DOCUMENTS 5,529,776 A    6/1996   Osther et al. ............ 424/160.1
6,168,953 B1 * 1/2001  Dropulic et al. ............ 435/455

OTHER PUBLICATIONS

LI et al., "Labeling Monoclonal Antibodies . . . " Bioconjugate Chemistry, 1994, Vol 5, No 2, pp 101–103.

Lewis et al. ". . . Modification of Proteins with DOTA . . . " Bioconjugate Chemistry, 1994, Vol 5, No 6, pp 565–576.

* cited by examiner

*Primary Examiner*—Dameron L. Jones
(74) *Attorney, Agent, or Firm*—John R Casperson

(57) ABSTRACT

A composition of matter comprises a pathogen-targeting organic moiety which is conjugated to a radioisotope which has a half-life of less than 100 days. The composition can be synthesized by bringing together a radioisotope having a half life of less than 100 days with a greater than stoichiometric amount of a complexing agent so as to form a first mixture containing a reaction product between the radioisotope and the complexing agent; removing the excess complexing agent from the mixture; and bringing together the first reaction product and an antibody substance so as to form a second mixture containing a reaction product between the first reaction product and the antibody substance. The composition is deposited on a particulate substrate and is useful for treating infectious diseases caused by pathogens by passing the patients blood through a bed formed from the particles.

9 Claims, No Drawings

EXTRACORPORAL SYSTEM FOR TREATING DISEASE WITH RADIONUCLEOTIDES

CROSS REFERENCES TO RELATED APPLICATIONS

This application is a continuation-in-part of copending application Ser. No. 09/183,454, filed Oct. 30, 1998, now allowed, and incorporated by reference herein.

BACKGROUND OF THE INVENTION

This invention relates to the delivery of radioisotopes to a disease-causing pathogen using a pathogen-targeting material conjugated to the radioisotope.

It is known to deliver cytotoxic radioisotopes to the nucleus of a tumor cell using a targeting protein or polypeptide conjugated with a radio-labeled nucleic acid-targeting small molecule. See, for example, U.S. Pat. No. 5,759,514. However, other than in the above referenced application, the use of radioisotopes to destroy disease-causing living pathogens such as bacteria or viruses has not heretofore been suggested.

Some strains of bacteria and viruses are very resistant to conventional drug therapy and are capable of killing or seriously debilitating the patient. Some strains are capable of mutating into a predominantly drug resistant form during the course of drug treatment, resulting in the death or debilitation of the patient. The widespread use of a particular drug treatment furthermore favors the genetic selection of strains which are resistant to that particular course of treatment. The presence of drug resistant strains of bacteria and viruses poses a growing world wide health threat.

A method for treating patients which have been infected with a drug-resistant pathogen would be very desirable. A technique for performing such treatment in a manner that minimizes the degree to which patients are exposed to a radioisotope would be even more desirable.

SUMMARY OF THE INVENTION

One embodiment of the invention provides a composition of matter suitable for use to treat disease in an extracorporal treatment technique. The composition comprises a conjugate of a living pathogen-targeting organic moiety coupled to a radioisotope which has a half-life of less than 100 days on a suitable support.

Another embodiment of the invention provides a method for treating an infectious disease caused by living blood-borne pathogens in a mammal. The process is conducted by obtaining antibodies from the mammal, replicating the antibodies to produce replicated antibodies, conjugating the replicated antibodies with a radioisotope which has a half-life of less than 100 days to produce a conjugate, fixing the conjugate to a conjugate support to form a supported conjugate, and passing the blood of the mammal into contact with the supported conjugate to bring the conjugate into contact with said living pathogens.

A further embodiment of the invention provides a method for treating an infectious disease caused by living blood-borne pathogens in a mammal. The method is carried out by identifying the blood-borne pathogens causing the infectious disease, selecting a supported conjugate comprising a particle support bearing an organic moiety which is chemically selective for attachment to said living pathogens and which is conjugated to a radioisotope which has a half-life of less than 100 days, flowing the blood of the mammal through a bed formed from particles of said supported conjugate, so that said blood-borne pathogens become associated with said radioisotope while in the bed, forming treated blood, and returning the treated blood to the mammal.

DETAILED DESCRIPTION OF THE PREFERRED EMBODIMENTS

In one embodiment of the invention, there is provided a composition of matter comprising a living pathogen-targeting organic moiety which is conjugated to a radioisotope which has a half-life of less than 100 days and is deposited on a particulate substrate such as beads to facilitate an extracorporal treatment of the patient's body fluid, such as blood.

Recent evidence has shown that radioisotopes which emit alpha, beta, or gamma radiation, and especially those of fairly short half-life and which emit Auger electrons during the decay process may be useful for inducing receptor cell specific cytotoxicity.

When a radioisotope decays by orbital electron capture or internal conversion, inner atomic shell vacancies are created in the residual atom. This highly excited atom attains a stable electronic configuration rapidly in a time scale of about $10^{-15}$ seconds via radioactive and non-radioactive transitions. In general, Auger, Coster-Kronig and super Coster-Kronig processes dominate the atomic vacancy cascades. As a result, numerous electrons are ejected from the atom and most of these Auger electrons have very low kinetic energies (about 20–500 eV) with extremely short ranges (a few nanometers) in water. Even though the energy carried by each of these electrons is only a small fraction of the total energy released in the decay process, their collective energy deposition is extremely high. Hence when the decays occur in the immediate vicinity of the critical biological molecules such as DNA, intracellular transmitters or any of the apoptotic cascade mechanisms, the biological effects to that cell are expected to be devastating.

Usually, radioisotopes used in accordance with the invention will have a half-life in the range of from about 1 to about 10 days. Preferably, the radioisotopes emit Auger electrons. Examples of suitable radioisotopes are Phosphorus 32, Copper 67, Gallium 67, Bromine 77, Yttrium 90, Technetium 99, Indium 111, Iodine 125, Iodine 131, Rhenium 186, Rhenium 188, Platinum 195, Bismuth 213, and Astatine 225. Of these, Copper 67, Yttrium 90, Indium 111, Rhenium 186, and Platinum 195 are preferred because these radioisotopes have distinct cytotoxic properties which may be exploited for therapy by the biologically directed targeting.

Compounds that are labeled with Auger electron emitters are most effective when the compound is internalized within or attached to the cell in a manner capable of activating apoptosis. Auger electrons provide very high-energy emissions but do so over a very short distance or action, which is less than 10–20 microns. This allows for an Auger emitting radioisotope to bring a high energy destructive force into areas to cause critical DNA strand damage (mitochondrial or nuclear). This, in turn activates the mechanism of apoptosis. Therefore, for a radioisotope-ligand to be a particularly desirable therapeutic agent, the compound must have a high cell to be destroyed-to background tissue ratio, a high therapeutic ratio and pharmacokinetic biodistribution profiles that optimize receptor binding, ligand internalization and cellular retention. The effects, therefore, of Auger electron emitters depend upon their cellular and sub-cellular location, which is governed, in turn, by the chemical form of the molecular agent (bioactive substance) to which the radioisotope has been attached.

Generally speaking, the living pathogen-targeting organic moiety is in the form of an antiviral, antifungal or an antibacterial antibody, although fragments of such antibodies or antibiotics which function to selectively carry the radioisotope into or onto a targeted pathogen are also considered suitable. Viruses, fungi bacteria, or prions may be selected as targets by appropriate selection of the organic moiety. Usually, the organic moiety has a surface chemistry which associates with a surface chemistry of the targeted pathogen. More preferably, the organic moiety has a surface chemistry to associate with a unique surface chemistry of the targeted pathogen.

Circulating antibodies normally recognize an antigen in the serum or tissue fluids and, furthermore, there are five identifiable classes: IgG, IgA, IgM, IgD and IgE. In addition to antigen binding, all antibodies exert other specific biological activities. The antigen-binding site is usually one in which there is a Fc fragment and two-antigen binding FAB fragments. X-ray crystallography and electron microscopy has provided the structural and biochemical organization of these moieties. Disulfide bonds predominate in cross-linking many of these domains. The primary function of any antibody is to bind any recognizable antigen. Recently, libraries of human specific antibody variable genes have been constructed for recombinant filamentous phages, which display the antibodies on their surface, and it is possible to select from high affinity antibodies for any chosen cell surface antigens from these libraries Phage antibodies that bind to a particular antigen may be separated from non-binding phage antibodies by antigen selection and the bound antibodies are recovered by elution. Repeated rounds of selection can isolate antigen-binding phages that were present at the start of the process at frequencies of less than one in a billion.

One technique of producing a homologous population of antibodies of known antigen specificity, are known as hybridomas that are derived from a single B cells and are called monoclonal antibodies. Another technique for producing antibody molecules is named phage antibody or phage libraries. In this case, gene segments encoding antigen-binding variable or V domains of antibodies are fused to genes encoding the coat protein of a bacteriophage. A collection of recombinant phage, each displaying a different antigen-binding domain on its surface is known as a phage display library. Each phage isolated in this way win produce a monoclonal antigen-binding particle analogous to a monoclonal antibody. Genes encoding the antigen-binding site, which are unique to each phage, can then be recovered from the phage DNA and used to construct genes for a complete antibody molecule by joining them to gene segments that encode the invariant parts of an antibody. When these reconstructed antibody genes are introduced into a suitable host cell line, the transferred cells secrete antibodies with all of the desirable characteristics on monoclonal antibodies that are produced from hybridomas.

The antibody binds stably to its antigen as the antibodies recognize the surface features of the native folded protein antigen and the antibody molecules can thus be used to locate their target molecules accurately in single cells or in tissue sections.

Specific examples of bioactive substances that can be used as vectors for the radioisotopes include:

Biologicals

A. Antiviral antibodies—
  1. gp120 and gp41 for HIV virus,
   2. Anti elf-2 antibodies for vaccinia,
   3. Anti-gE/gl antibodies for herpes simplex 1 virus,
   4. Anti IL-10, or BHRF1 antibodies against the Ebstein-Barr virus,
   5. Anti E3 antibodies for adenovirus group.

B. Antibacterial antibodies—
   1. C3b, iC3b, MBL, certain oliosaccharides, and lectins are identifiable markers on gram positive and gram negative cell surfaces and thus serve as markers for vector antibodies.

C. Antibodies toward a unique family of proteins called STATs that also bind DNA.

D. Antibodies directed toward surface LMP-1 antigens that are found on the Ebstein-Barr infected cells, including the EB related papillomas.

E. Antibiotics: Rimafin, streptomycin, tetracycline, puromycin and cyclohemimide all attach to RNA initiation, transcription mechanism of the rapidly reproducing bacteria but Actinomycin D which binds directly to nuclear and mitochondrial DNA while the penicillins and cephalosporins bind directly to the chemokines of the cell wall of the infecting organism. Radioisotopes that are conjugated to an antibiotic would not only enhance the bactericidal but bacteriostatic properties of the drug and but would also reduce the change of drug resistant bacteria.

F. Nonspecific apoptotic antibodies to: Fas ligand, IVCE/CED-3 family, Bcl-2 family, NfkB, CD40L, CLTA-4, TNFR, APO, and TRAF family activate non-selectively the cell destructive mechanism or apoptosis Labeling of biologics with radioisotopes for diagnosis and therapy has usually been accomplished through the use of bifunctional chelating agents, which contain both a reactive functionality for covalent attachment to proteins and with a strong nucleotide binding group capable of forming a chemically stable complex with the radioisotope. In the invention, a living pathogen-targeting organic moiety is preferably covalently linked to a complexing agent which binds the radioisotope and the desired product from this coupling is deposited on a substrate. A preferred embodiment of the invention uses a bifunctional complexing agent having a reactive functionality covalently attached to the pathogen-targeting organic moiety and a strong nucleotide binding group forming a chemically stable complex with the radioisotope. The strong nucleotide binding group can be in the form of a chelating agent. Examples of suitable chelating agents which can be employed in the invention include ethylenediaminetetraacetic acid (EDTA), diethylenetriaminopentaacetic acid (DTPA), ethyleneglycol-0,0'-bis(2-aminoethyl)-N,N,N', N'-tetraacetic acid (EGTA), N,N'-bis (hydroxybenzyl)ethylenediamine-N,N'-diacetic acid (HBED), triethylenetetraminehexaacetic acid (TTHA), 1,4,7,10-tetra-azacyclododecane-N,N', N", N'"-tetraacetic acid (DOTA), 1,4,7,10-tetraazacyclotridecane-1,4,7,10-tetraacetic acid (TITRA), 1,4,8,11-tetraazacyclotetradecane-N, N', N", N'"-tetraacetic acid (TETA), 1,4,8,11-tetraazacyclotetradecane (TETRA) and their substituted derivatives. Of these, diethylenetriaminopentaacetic acid (DTPA) and 1,4,7,10-tetra-azacyclododecane- N, N', N", N'"-tetraacetic acid (DOTA) are preferred, because a method that we have modified and employed extensively for the radioactive labeling of bioactive molecules uses diethylenetriaminopentaacetic acid (DTPA) and DOTA as bifunctional chelates which may be achieved by using anhydride (mixed or cyclic) as acylating agents.

A preferred embodiment of the composition of matter can be synthesized by bringing together a radioisotope having a half life of less than 100 days with a greater than stoichiometric amount of a complexing agent so as to form a first mixture containing a reaction product between the radioisotope and the complexing agent; removing the excess complexing agent from the mixture; and bringing together the first reaction product and an antibody substance so as to form a second mixture containing a reaction product between the first reaction product and the antibody substance. Usually, the antibody substance comprises a protein and generally will comprise an immunoglobulin produced by mammalian cells in response to a living pathogen. The complexing agent has a first functional group which reacts with the radioisotope and a second functional group which reacts with a site on the immunoglobulin. Preferably, the first reaction product is ionically neutral, and the process further comprises flowing the first mixture though an anion exchange column to remove excess complexing agent from the mixture. The first reaction product is preferably brought together with a less than stoichiometric amount of the antibody substance to avoid overlabeling, which could reduce effectiveness or cause side effects.

Conventional labeling processes of protein based molecules with augur emitting gamma radioisotopes involves conjugation of the bi-functional agent to the biologic and then this process is followed up with labeling with a radioisotope. Our alternative method, which is called prelabeling, is one in which the bifunctional chelating agent is first radiolabeled and then conjugated to the biologic.

Radiolabeling of antibodies has conventionally been accomplished by prolonged incubation of the conjugate with a radioisotope solution at room temperature. This may, however, result in significant radiolysis of the protein, such as the antibody structure. Rapid and efficient incorporation of the radioisotope onto the bioactive vector (antibody) is demanded in order to afford a high yield and specific activity of the radiolabeled immunoconjugate.

The prelabeling procedure of the invention is defined in the following scheme and contains three basic steps:

1. Radioactive chelate formation in the absence of an antibody (vector)
2. Chelate purification
3. Antibody (bioactive vector) conjugation With the invention, any combination biologic or bioactive substance (vector) may be conjugated with an Auger emitting radio nucleotide. An exemplary procedure of prelabeling is as follows:

Step 1

A bi-directional chelating agent DOTA-Glys3-L (p-isothiocyanate)-Phe-amide was prepared. Carrier free radioisotope (Yt90 or In 111) in 0.05 M HCL was dried in a heating block under N2 and 100 uL of mM 1 in 0.2M ammonium acetate (pH 5.0) was added. This mixture was incubated at 37 degrees C. for 30 minutes and then 25 uL of 50 mM DTPA in 0.1M ammonium acetate, (pH 6.0), was added for 15 minutes at room temperature (to complex any remaining radioisotope). The solution was loaded into anion-exchange resin column and this column was spun for 2 minutes at about 2000 g, and this was followed by elution with four 125 uL aliquots of sterile purified water by centrifugation at about 2000 g each. Most of the radioactive chelates for step 2 are recovered in the first four fractions.

Step 2

All of the eluted fractions are collected and concentrated to about 15 uL with a speed-vac concentrator, a step that may be avoided when higher amounts of radioactivity are used.

The radiochemical purity of both Yt-90 and In-111 was determined to be greater than 9% by gel filtration HPLC, cellulose acetate electrophoresis and silica gel TLC. Excess chelating agents, complexes containing divalent nucleotides and DPTA complexes are negatively charged. Thus, the DOTA-peptide complexes with trivalent nucleotides can be filtered quickly through an appropriately designed anion-exchange column in water to separate them from anionic species. Thus the neutral chelate avoids the need for more complex processes, in step 2, such as HPLC with mixed organic/aqueous solvents. Prelabeling deals with the impurity problem by using a large excess of chelating agent and then removing this excess, but it does not eliminate trivalent nucleotide complexes from the product.

Step 3

In the conjugation step, a high concentration of antibody (bioactive vector) is desired. In this process each molecule of the chelate isothiocyanate will frequently encounter biovector amino groups with which to react. The concentrated solution is mixed with 1 mg of chimerical mAb (bioactive vector). The pH is adjusted to 9.5 using aqueous 2.0 M triethylamine. This mixture is incubated at 37 degrees for one hour and was isolated using a centrifuged gel-filtration column. At the chosen conjugation conditions of 1 hour incubation at 37 C, pH 9.5 the conjugate yield was over 40%, but for radioactivity yields of 100 mCi or greater radiolysis will become important. While the isothiocyanate group on the bifunctional chelating agent is potentially subject to hydrolysis during the labeling and conjugation steps, controlled experiments have demonstrated a loss of less than 5% of the isothiocyanate.

This procedure has several advantages over conventional radiolabeling of antibodies. In step one, the nucleotide chelate formation is easier to control because there is little or no competition form the nucleotide binding sites on the protein and the chelation conditions are not limited by the need to avoid denaturing the protein based antibody. In step 2, excess chelating agent may be removed before the radioactive chelate is attached to the protein, thus avoiding the production of multiply labeled immunoconjugates, each with unfavorable biological properties. Finally, in step three, the antibody is chemically modified and radiolabeled in one step, thereby minimizing the chemical manipulation of the antibody and reducing losses of the radiolabeled antibody chelate. This prelabeling approach permits the use of a large excess of bifunctional chelating agent to achieve a high chelation yield quickly in step one, but it requires a rapid purification method to remove unlabeled reagent in step two.

Radiolabeling of protein conjugates with radioisotopes is sensitive to pH, buffer and temperature effects. The optimum pH for the labeling (step 3) reaction was different for each protein and may be related to the isoelectric point of the protein. Radioisotope incorporation at high specific activity was accomplished in acetate and Tris buffers, while the presence of citrate inhibited the labeling reaction. Increasing the temperature of the radiolabeling reaction to 37–43 degrees greatly increased the efficiency or radioisotope incorporation and the kinetic stability of the radioconjugates.

The chelates that are used for labeling comprise less than 5% of the total attached chelates on the Ab (bioactive vector). In conventional methods of labeling, the excess chelating groups may affect the biological properties of the antibodies by inducing an immune response and impure radioisotope solutions may require larger amounts of the immunoconjugate. With prelabeling, however, a far smaller number of chelates become attached to the antibody and practically all are radiolabeled while the number of multiply modified antibodies is essentially zeroed. These radiolabeled antibodies are nevertheless fully immunoreactive. The efficiency of incorporating a radioisotope into a bioactive chelate is directly proportional to the pH, for example the incorporation increased form 69% at pH 5.5 to 81% at pH 7. The immunoreactivity of radiolabeled Indium 111 and Yttrium 90 onto antibodies was found to be 98.6%. Covalent attachment of DOTA to amines by acylation with the isobutyl formate mixed anhydrides of the chelating agent has been employed to synthesize a variety of DOTA amines. A simple water soluble chemical procedure for the conjugation of DOTA to proteins, by ester attachment, is enhanced by elevated temperature (37–43 degrees), optimum pH (7–9) and appropriate buffer solutions which result in the rapid labeling of radioimmunoconjugates displaying a high specific activity.

The common factor in the use of one of these Radionucleotide 1-DOTA or DPTA (chelators)-biovectors-antibody complexes described above is that it attaches only to the surface of the target cells(s) to be destroyed and the emission of Auger energy (Indium 11 or Yttrium 90) is transmitted in tissue only for short distances (10 nm–15 nm) and duration (2–3 day half-life), this activating one of the apoptotic cell destruction mechanisms. The process of apoptosis and cell lysis is pivotal in the explication of the role of induction of antigen/antibody-conjugated-radioisotope triggered cell death using of new created radiolabeled monoclonal/phage antibodies (mAbs).

There are two treatment methods according to the invention. In the first method, the antibodies produced in response to the living pathogens are obtained and replicated. The replicated antibodies are conjugated with a radioisotope which has a half-life of less than 100 days to produce a therapeutic composition. The therapeutic composition is then brought together with the pathogens outside of the patients body. The second method is carried out by identifying the living pathogens causing the infectious disease, selecting a therapeutic composition comprising an organic moiety which is chemically selective for attachment to the pathogens and which is conjugated to a radioisotope which has a half-life of less than 100 days, depositing the therapeutic composition on support particles, forming a bed of the support particles, passing the patients blood through the bed, and reintroducing the patient's blood to the patient. In this manner the pathogens become attached to the therapeutic composition so that they receive a fatal radiation dose.

The preferred radioisotopes to use are those which emit Auger electrons, and in both methods the organic moiety is generally an antibody substance, usually an immunoglobulin or immunoglobulin fragment. The antibody substance is usually conjugated to the radioisotope with a complexing agent as hereinbefore described. The dose to be administered to the pathogens will vary depending on many factors, but will generally be in the range of 1 to 1000 millicuries and in an amount which is adequate to render at least some of the pathogens nonviable.

The invention can be applied to treat disease caused by the Human Immunodeficiency Virus, HIV, the retrovirus that causes AIDS. The virus is a double stranded RNA virus 100–120 nm diameter and as its basic structure it has a gag (core protein-p24 and matrix protein-p17 and p7), pol (polymerase/reverse transcriptase-p66/51, p32 and p11) and env (envelope protein) genes. On the surface of the virus are two glycoproteins called the gp 120 and a trans membrane gp 41. The gp120 is responsible for binding to the surface of uninfected CD4 cells (T lymphocytes) by a GP120-CD4 linkage. In fact, the HIV gp120 glycoprotein binds to CD4 resulting in a conformational change that exposes the V3 loop in gp120 and permits the subsequent interaction with a chemokine receptor CXCR4 on the surface of CD4 T cells or CCR5 surface receptor on macrophages in order to gain entry into these cells. Therefore, these chemokine co-receptors are critically involved in the subsequent gp41-mediated fusion and cell internalization. There is widespread immune dysfunction and the host CD4 cells are killed as the virus replicates using the reverse transcriptase as mechanism to usurp the CD4 cell's own DNA. The spectrum of immune dysfunction is characterized by depletion of the CD4 T cells, decrease responses to antigens, mitogens, alloantigens and anti-CD3 antibody, a associated with decreased IL-2 production as well as other changes in cytokine production. Finally there is a loss of specific HIV cytotoxic responses and an increase in unresponsive CD8 T cells, increased beta-2 microglobulin and serum neopterin as well as an increase in autoantibodies and immune complexes. The average half life of the virus and other infected cells in the circulation is less than two days, wherein millions of virions are released from infected cells and similar numbers of new cells are infected daily. Antibodies to core and surface proteins may be detected in the serum of infected patients within 2–6 weeks after the initial infection has occurred. Traditional therapy has been nucleoside analogue reverse transcriptase inhibition and polytherapy with non-nucleoside reverse transcriptase inhibitors and carbocyclic nucleoside analogues. Even with aggressive triple-drug combination anti-retroviral therapy, a decrease in HIV-RNA (viral load) plasma levels may not be sustained, and this indicates viral therapy failure. HIV resistance to anti-retroviral agents is likely to be a significant factor contributing to treatment failure in many individuals. This resistance to drug therapy develops because of the error rate of the HIV reverse transcriptase and the high replicative rate of the HIV which leads invariably to frequent mutations in the HIV genome. Resistance to most anti-retroviral agents has been documented in both in vitro and in vivo. There are mechanisms to test for resistance mutations (genotype analysis) or resistance phenotype for virus from any given HIV infected individual and cross-resistance is known to occur.

The HIV virus envelope glycoproteins are less than ideal immunogens since the gp120–gp41 are associated and are buried in the interior of the functional envelope glycoprotein spike outer core. The non-covalent nature of the association between gp120 and gp41 contributes to the lability of the functional envelope glycoprotein titer. Furthermore, the CD4 binding site is recessed and variable regions, which exhibit glycosylation, flank it. Moreover, variable loops, V2 and V3 mask the chemokine receptor-binding site. However, during the natural HIV infection, disassembled envelope glycoproteins elicit most of their antibodies directed toward these viral envelope components. At that time the interactive regions of gp120 and gp41 are particularly antigenic. However, because the cognate antibodies cannot bind the assembled, functional envelope glycoprotein complex, these natural antibodies do not exhibit an effective neutralizing activity. The efficacy of the humoral immune response in vivo is compromised by at least two factors: the relative resistance of primary virus isolates to neutralization and the temporal pattern with which neutralizing antibodies are generated. HIV viruses that have been passaged in immortalized cells lines are typically more sensitive to neutralization by antibodies than are primary clinical isolates. During natural HIV infections, disassembled envelope glycoproteins elicit most of the antibodies directed to these viral components. Antibodies to these envelope proteins typically can be detected in the sera of HIV infected individuals by 2–3 weeks after infection. Later in the course of the HIV infection, antibodies capable of neutralizing a wide range of HIV isolates appear. Human monoclonal antibodies derived from HIV infected individuals have been identified that recognizes the gp120 proteins from a diverse range of HIV isolates. Another fairly conserved gp120 neutralizing epitope is recognized by the 2G12 antibody and bind the gp120 epitope on the outer domain. This 2G12 antibody may recognize more conserved carbohydrate structures that have been formed as a result of a heavy concentration of N-linked glycosylation in the gp120 outer domain. In vivo, the apparent rarity with which the 2G12 antibodies are elicited attests to the success of the viral strategy of using heavily glycosylated outer domain surface in immune evasion. The use of phage 2G12, gp120 and gp41 antibodies will avoid many of the bioactive vector problems.

By exploiting strategies used by the immune system, phage libraries can produce antibodies with many clinically applicable immunochemical specificities. From such libraries, many different antibodies can be isolated against virtually any antigen. Phage antibodies have a number of advantages over monoclonal antibodies produced from hybridomas. First the amino acid sequences of the antibodies are entirely human. Second, in vivo mechanisms that normally get rid of self-reactive antibodies are avoided, because selection occurs mainly in vitro. This makes it possible to produce human antibodies against human antigens. Third the immunoglobulin V genes are already cloned and this increases the affinity of the antibodies, change their fine specificity, and alters their size or valency. Finally, for this purpose, genetic engineering may be used to fuse the antibodies to cytolytic proteins that enhance the therapeutic effect of the antibodies. The ability to produce these phage antibodies is relatively rapid (a few weeks). Therefore, phage antibodies to gp120 and gp41 could be chelated to a radioisotope with a half-life of 2–3 days such as 100 millicuries of Indium 111 (half-life of 2 days) should be given intravenously to AIDS patients. The course of the RNA viral load, CD4 and CD8 T lymphocytes as well as other markers heralds both the progression and the regression of disease. This potentially curative extracorporal treatment procedure should be repeated every 4–6 months, while the response of therapy is scientifically evaluated.

The Patients

Human subjects who are good candidates for treatment in accordance with the invention are those who are afflicted with blood-borne pathogens which are debilitating and have been unresponsive to conventional therapies.

In the case of HIV infection, the patient should meet the following criteria:

1. The patient should be 18 years of age or older and confirmed with AIDS. The patient should have a positive ELISA and Western Blot test for HIV infection.
2. The course of AIDS has been either poorly controlled or unresponsive to adequate anti-HIV therapy as confirmed by clinical evaluation, an RNA viral load of over 10,000 and a CD4 T cell count of over 250. Patients who are incapable of generating a cellular response following a significant reduction of RNA viral load are not considered to be good candidates.
3. The patient has at least 2 or more HIV positive test results with a viral RNA load of over 10,000.
4. The patients is currently stable (for at least 12 weeks) but exhibits poor or no response to anti-viral therapy (viral load increasing and/or CD 3, 4, 8 counts decreasing).
5. The patient should have adequate bone-marrow (hematopoietic) function as shown by the following:
    a. Peripheral absolute granulocyte count of 1500/microliter or greater or a total leukocyte count of 3500/microliter or greater.
    b. Platelet count of 75,000/microliter or greater.
    c. Hemoglobin (Hb) and Hematocrit (Ht) at least 60% of normal
6. The patient should have adequate hepatic function as shown by the following:
    a. Serum bilirubin of 2.0 mg/dl or less
    b. Values for SGOT(glutamate oxalacetate transarinase), SGPT(serum glutamate pyruvate transaminase) and alkaline phosphatase of not more than three time the normal range.
7. The patient should have adequate renal function as shown by a serum creatinine of 2.0 mg/dl or less.
8. The patient should not be impaired to the point of being disabled, requiring special care and assistance, having severe signs and symptoms, and having abnormal Laboratory.

HIV positive (HART Failure-AIDS) patients are preferred.

The patient is not a good candidate is if any of the following apply.

1. The age of the patient is less than 18 years.
2. The patient has a hemoglobin value of less than 8 gm/dl
3. The patient has clinically significant abnormalities in glucose, sodium, potassium, chloride, calcium, phosphorus, uric acid, or BUN.
4. The patient as Participated in an investigational clinical trial or treatment within the previous 30 days;
5. The patient has other medical condition in which the study may pose a threat to the patient Preparation of the Pharmaceutical
Radiometal and Antibodies In accordance with the invention, a radiometal is conjugated with an antibody for the target blood borne pathogen.

The Radiometal

For AIDS treatment, Iodine 131, which is suitably employed in this application, can be obtained from M.D.S. Nordion with a certifiable purity of 99.2% and impurities of 0.2%. The batch, validity number and date are recorded. Following receipt the product is analyzed for impurities by atomic emission spectra and any impurities are removed by gel filtration with an appropriate chelating agent and final product is then tested for purity.

The Antibody

For AIDS treatment, suitable antibodies can be obtained from Research Diagnostics, Inc. HIV gp 120, a recombinant human cell derived antibody having a molecular weight of 120,000 Daltons is lyophilized and is of isotype IgG1 produced in Baculovirus system and binds to HIV-1 gp 120 envelope antigen on the V 3 loop, but it does not neutralize the HIV-1 MN, HIV-1SP2, HIV-IIIRF or the HIV-1SF2.

Forming the Antibody-radiometal Conjugate

Iodine 131 binds directly to the tyrosine aromatic ring 1,5 positions of the gp120 antibody in-vitro. Therefore, recombinant gp 120-antibodies are labeled with Iodine 131 by direct incubation chemical reaction. The following mixture I 131-gp120 antibody is tested for bound and unbound I 131 and the latter (unbound 1 131) is eluted from the g

Adherence of the Conjugate to a Suitable Support

After I 131 and gp120 binding the radioactive compound is then reacted with Protein A or Protein G coated 100–500 mm beads and the excess I 131–gp120 antibody-compound is washed and passed over an anion-bound resin for removal of traces of antibody-I 131 compound. The resultant beads bind the antibody-I 131 compound in their Fc portion, which correctly orients these antibody complexes for maximum antigen (gp120/antigen on the HIV viral plasma membrane surface) trapping and capture. Protein G captures more antibody subclasses than the Protein A and is therefore preferred for this application.

Stability Testing of the Conjugate

A test is performed to verify the stability of the conjugate under the conditions within the canister by taking an aliquot (10–50 microliters) of the radiolabeled conjugate containing approximately 8×10(6) cpm of I 131 radioactivity and adding the conjugate to 1.1 milliliters of fresh human serum containing 10 microliters of 10% $NaN_3$. The mixture was incubated at 37 degrees Centigrade throughout the study, during which 100-microliter samples of serum were analyzed by gel filtration BPLC on two Pharmacia Superose 12 HR 10/30 columns (1×30 cm) in series, using an isocratic mobile phase of 0.05 M $Na_2SO_4$, 0.02 M $NaH_2PO_4$, 0.05% $NaN_2$, at pH 6.8. Serum samples are analyzed at intervals ranging from 15 to 72 hours for 10 days to determine conjugate stability.

Preparation of a Treatment Bed Containing the Conjugate

The beads are placed in a canister that allows whole blood to freely pass through the pores in the canister but without allowing the beads to escape. Generally speaking, the bed contains on the order of 100 mCi of I-131 or other radioisotope bound to approximately 10 micrograms of antibody, via tyrosine residues, for example. The conjugate is attached to the beads via a protein, for example, which binds to the substrate to the antibody. Functionally speaking, the bed preferably contains adequate conjugate to bind 98% or more of the blood borne pathogen in the patient's blood in three passes of the patient's blood volume through the canister. This is preferably accomplished in a period of a few hours.

Use of the Treatment Bed

Whole heparinized-blood is used into the extra-corporal device. A double lumen IV catheter is inserted in the FHV positive patients. Peripheral blood will be analyzed before and after the whole blood-pheresis. The catheter is connected to the device and the flow rate is adjusted to 500–1000 milliliters per hour or about 2–4 drops per second. This rate allows for complete exchange to occur in 8 to 10 hours and during the 7–8 day period of whole blood exchange, a passage of 21 times through the canister. Continuous monitoring of the radiation exposure will be made during the procedure. Each patient will be placed on the whole blood I 131-gp120 antibody dialysis for 8 days in out patient therapy (renal dialysis) unit. Renal dialysis may be performed for a period of 30 or more days if necessary, without untoward effects.

Theory

Specific and unique preceptors (located on the surface of all living cells) are on targeted celled as unique membrane antigens (usually glycoproteins that extend from the cell membrane surface) that are employed for the targeted cell to attach to normal cells. They are called intgrins, selectins and adhesion molecules. Recombinant lyophilized monoclonal antibody is obtained against these specific and unique antigens. A radiometal of suitable half-life and intensity is selected for emitting energy during the life cycle of the targeted cell. A radionucleotide-monoclonal antibody is formed from these components for use in treating the blood of the patient.

In the case of HIV/AIDS it is known that the AIDS virus has a life cycle of 48 hours in humans and there is neither a known cure nor an adequate animal models for simulation of the human HIV disease. When the radiometal (Iodine 131) is bound to the HIV cell surface antibody (gp120), which in turn, attaches to the HIV cell surface antigen, the radiometal will destroy the gp 120 antigen and the virus itself. Lymphocyte adaptive response is likely to occur following therapy or destruction of the HIV virus.

The Gp 120 viral antigen normally is hidden but prior to attachment and immediately after exit (virions) it is exposed. The V3 loop is the active attachment to the CD4 marker on the host T lymphocyte. The GP 120 monoclonal antibody has 22 tyrosine linkages on the V1, V2, V4, and V5 loops, but none on the V3 loop. The binding of binding of I 131 occurs chemically with the tyrosine linkages. The binding to tyrosine is firm and not easily capable of dissociation. For example, I 131-tyrosine binding is used in thyroid irradiation.

The recent development of an efficient process of biological chelating allows for the adherence of antibodies to a radiometal, and makes it possible to produce compounds that are both targeted because the antibody is specific for only one antigen on the cell surface and delivers the potential destructive fore (Iodine 131 gamma emission) in water and tissue.

For application of the invention, the measurement of the I 131 isotope in free form is easily performed. The measurement of the effect of the treatment on the patient is also readily performed.

Technology for extra-corporal therapy is standard medical practice in the dialysis and plasmapheresis fields. Technology exists for antibody (gp 120) capture (on beads or columns) is available using Protein A or Protein C coating.

The gp 120 antibody/I 131 binding to the HIV viral gp 120 antigen (receptor) follow the accepted formula for peptide-receptor binding. Generally speaking, the affinity for a peptide with its receptor may be seen in the following formula:

$$(PR)/P+R=K\times M$$

where P is the circulating peptide, in this case gp 120-I 131

R is the peptide specific receptor, in this case Viral gp 120 receptor,

PR designates the peptide bound to the specific receptor,

K is the affinity constant, and

M is the weight in grams of a single peptide molecule.

If r is express as the micrograms of gp 120-I 131 bound to viral protein gp 120 antigen M.

As there are independent binding sites on each virus (gp-120 antigens) these may be assigned as v. Therefore, $$r=v(K-gp120\text{-}I131)/1+(K-gp120\text{-}I131).$$

since the binding sites on the viral gp 120 are all of the same class and chemical structure a and molecular configuration.

The mathematical formula may be derived from a standard Langmuir plot as:

$$r=\text{Sigma}(n-1)VK(gp120\text{-}I131)/1+K(gp120\text{-}I\ 131)+v\eta K\eta(gp120\text{-}I131)$$

For gp 120 antibody-viral gp120 antigen, this affinity may be measured and is very high, on the order of 1.9933 ($10^{20}$).

Specific Methods The recombinant HIV-1 glycoprotein gp 120 antibody is bound to Iodine 131 (half life 8.02 days) in the following concentrations:

a) 0.5 mCiI 131 MDS Nordion
b) 1.0 mCiI 131
c) 2.0 mCiI 131
d) 5.0 mCiI 131

The method of measurement for effectiveness of therapy is amply discussed herein.

The measurement of radioactivity of pre and post therapy lines and peripheral blood of the patient may be immediately determined and, if necessary, the therapy may be discontinued.

A dose response curve may be evaluated and repeat therapy may be performed as needed.

The following schedule will be maintained following consent has been obtained.

Each patient will have a double lumen intravenous catheter placed in the appropriate and initial sample of blood drawn for the initial baseline CD3, CD4, CD8, CD38, RNA viral load, DNA flow studies. Following these initial studies, each extra-corporal system of slow infusion over the I 131 0.5–5m Ci-gp120 antibody-beads over a period of 192 hours (8 days).

On the basis of these methods, the most appropriate dose of Iodine 131-gp120 monoclonal antibody beads can be produced with verifiable quality control.

Because of the variables for prognostication for AIDS therapy, which includes rapid mutation of the HIV virus, the host response and the host reservoirs (dendritic cells, macrophages and semen) it is probable that, if successful, additional extra-corporal therapy may be necessary. During the course of follow-up evaluations, it may be necessary to repeat the therapy with the objective of reducing the RNA viral load to undetectable levels and with gradual individual improvement of CD3, CD4, CD8 counts to normal levels.

The patient will return to Out Patient Suite for insertion of the double lumen catheter and for slow extra-corporal venous infusion of heparinized whole blood over extra-corporal columns of isolated radioactive beads of Iodine 131-gp120/41 antibodies over 192 hours (8 days).

What is claimed is:

1. A method for treating an infectious disease caused by living blood-borne pathogens in a mammal, wherein said mammal produces antibodies in response to said living pathogens, said method comprising obtaining antibodies from said mammal;

replicating said antibodies to produce replicated antibodies, conjugating said replicated antibodies with a radioisotope which has a half-life of less than 100 days to produce a conjugate, fixing said conjugate to a conjugate support to form a supported conjugate, and passing the blood of said mammal into contact with said supported conjugate to bring said conjugate into contact with said living pathogens and form treated blood which is passed back into circulation in said mammal.

2. A method for treating an infectious disease caused by living blood-borne pathogens in a mammal, wherein said mammal produces antibodies in response to said living pathogens, said method comprising obtaining antibodies from said mammal;

replicating said antibodies to produce replicated antibodies, conjugating said replicated antibodies with a radioisotope which has a half-life of less than 100 days to produce a conjugate, fixing said conjugate to a conjugate support to form a supported conjugate, and passing the blood of said mammal in contact with said supported conjugate to bring said conjugate into contact with said living pathogens, wherein said supported conjugate is in the form of particles, said method further comprising forming a bed of said particles, flowing the blood of said mammal through said bed to form treated blood, and returning the treated blood to said mammal.

3. A method as in claim 2 wherein the mammal is a human and the pathogen is HIV virus.

4. A method as in claim 3 wherein the antibody is selected from the group consisting of gp120 antibody and gp2G12 antibody and the radioisotope is Iodine 113.

5. A method for treating an infectious disease caused by living blood-borne pathogens in a mammal, said method comprising identifying the blood-borne pathogens causing the infectious disease, selecting a supported conjugate comprising a particle support bearing an organic moiety which is chemically selective for attachment to said living pathogens and which is conjugated to a radioisotope which has a half-life of less than 100 days, flowing the blood of said mammal through a bed formed from particles of said supported conjugate, so that said blood-borne pathogens become associated with said radioisotope while in the bed, forming treated blood, and returning the treated blood to said mammal.

6. A method as in claim 5 wherein the organic moiety is selected from the group consisting of an immunoglobulin and an immunoglobulin fragment.

7. A method as in claim 6 wherein the radioisotope emits Auger electrons.

8. A method as in claim 5 wherein at least some of the living pathogens are rendered non-viable while in the bed.

9. A method as in claim 8 wherein the living pathogen is a virus.

* * * * *